(12) United States Patent
Dunn

(10) Patent No.: US 10,578,596 B2
(45) Date of Patent: Mar. 3, 2020

(54) BETA-PHASE INDICATOR

(71) Applicant: ElectraWatch, Inc., Charlottesville, VA (US)

(72) Inventor: Ryan C. Dunn, Charlottesville, VA (US)

(73) Assignee: ELECTRAWATCH, INC, Charlottesville, VA (US)

( * ) Notice: Subject to any disclaimer, the term of this patent is extended or adjusted under 35 U.S.C. 154(b) by 149 days.

(21) Appl. No.: 15/643,467

(22) Filed: Jul. 6, 2017

(65) Prior Publication Data

US 2018/0128796 A1     May 10, 2018

Related U.S. Application Data

(60) Provisional application No. 62/359,167, filed on Jul. 6, 2016.

(51) Int. Cl.
    *G01N 33/20*     (2019.01)
    *G01N 31/22*     (2006.01)

(52) U.S. Cl.
    CPC ........... *G01N 31/221* (2013.01); *G01N 33/20* (2013.01)

(58) Field of Classification Search
    None
    See application file for complete search history.

*Primary Examiner* — Paul S Hyun
(74) *Attorney, Agent, or Firm* — Paul A. Bell

(57) ABSTRACT

A quick, non-destructive and inexpensive test is disclosed to determine whether a portion of a structure made of 5XXX Aluminum alloy is sensitized. Unlike the current sensitization tests, this test can be performed by non-skilled personnel without complicated procedures and equipment. Since the test is non-destructive, it does not require the removal material from the structure. This feature makes the test particularly attractive for in situ applications such as for use on existing structures like ships. The test requires the application of an indicating chemical to the surface of the material being tested. The indicating chemical has a predetermined pH which may be either acidic or alkaline. The indicating chemical also contains an pH indicator of predetermined value. After a short period of time has elapsed, the percentage of pH color change observed from the indicating chemical can be used to determine whether the sample is sensitized or not. It is also possible to obtain at least an approximation of the Degree of Sensitization of the structure using the test.

9 Claims, 5 Drawing Sheets

BETA-PHASE INDICATOR

CROSS-REFERENCE TO RELATED APPLICATIONS

This application claims the benefit under 35 U.S.C. 119(e) of commonly owned U.S. patent application 62/359,167 filed on 6 Jul. 2016.

STATEMENT REGARDING FEDERALLY SPONSORED RESEARCH OR DEVELOPMENT

Not applicable.

SEQUENCE LISTING

Not Applicable.

FIELD OF THE INVENTION

The present invention relates generally to the field of testing an Aluminum-Magnesium alloy for sensitization.

BACKGROUND OF THE INVENTION

To maximize the stability and, in some cases, speed of naval vessels, 5XXX aluminum-magnesium alloys are often used to construct ship superstructures and more recently the hull and superstructure of certain naval vessels [e.g. the Independence variant of the U.S. Navy Littoral Combat Ships]. It is a well-known fact in Naval Architecture that every pound of structure that can be eliminated above the ship's metacenter will increase a ship's stability. It is equally well-known that every pound of structure that can be eliminated from the overall ship's weight will increase the overall efficiency of the ship.

The primary metal, aluminum, offers the advantage of being lightweight. Adding magnesium to the aluminum creates an alloy that is both lightweight and strong. To understand how sensitization, intergranular corrosion (IGC), and stress corrosion cracking (SCC) impact a naval vessels constructed from 5XXX aluminum, the composition and basic material properties of 5XXX aluminum alloys need to be explained.

The primary alloying element in 5XXX aluminum (Al) alloys is magnesium (Mg). During production of the alloy, highly controlled heat treatments are used to evenly distribute magnesium (Mg) in the aluminum (Al) matrix. Different alloys in the 5XXX series contain varying amounts of Mg ranging from ~3.5% in 5086 to ~4% in 5083 up to ~5% in 5456. The evenly distributed state of the Mg within the Al matrix is thermodynamically metastable and exposure to even mildly elevated temperatures for extended periods of time will cause the magnesium to form beta-phase ($Mg_2Al_3$) precipitates. The formation of these beta-phase precipitates along the grain boundaries as a connected network is called sensitization. A structure made from a 5XXX-series alloy which has been sensitized contains a connected network of beta phase precipitates along the grain boundaries.

The rate of sensitization is primarily a function of five factors: thermal exposure, alloy composition (% Mg), material temper, grain size, dislocation density and microstructure. Assuming equivalent thermal exposures, tempers, grain sizes, dislocation densities and microstructures; 5XXX Al alloys containing higher amounts of magnesium will sensitize faster than 5XXX Al alloys with lesser amounts of magnesium. For example, 5456 (~5% Mg) will sensitize faster than an equivalent 5083 (~4.0% Mg) sample, and 5083 will sensitize faster than an equivalent 5086 (~3.5% Mg) sample when exposed to the same thermal conditions.

The beta-phase ($Mg_2Al_3$) precipitates contain approximately 38% Mg which is significantly higher than the Al matrix, which for Al 5456 contains only approximately 5% Mg. Elemental Mg is thermodynamically less stable and kinetically more active than elemental Al. These characteristics make Mg more susceptible to dissolution in low and neutral pH environments. The beta-phase ($Mg_2Al_3$) behaves more like Mg than Al and will dissolve rapidly in seawater environments. This difference in dissolution behavior, combined with the fact that beta-phase preferentially forms on grain boundaries during service, leads to the preferential corrosion of those grain boundaries, which is termed intergranular corrosion (IGC).

Stress corrosion cracking will occur if a specific set of material properties and environmental conditions are present. Sensitized material is one of the conditions that contributes to SCC of aluminum alloys. The sensitized material then needs to be exposed to a corrosive environment and IGC needs to initiate corrosion along grain boundaries. Lastly, a tensile stress needs to be applied to the IGC affected material to form a stress corrosion crack. It should be noted that material sensitization alone does not result in stress corrosion cracking. For example, there have been instances on flight decks of U.S. Navy Guided Missile Cruisers where flight deck material has tested as sensitized but the lack of significant tensile stresses has historically not resulted in stress corrosion cracking problems in this area. The relationship between sensitization, intergranular corrosion (IGC) and stress corrosion cracking (SCC) is illustrated in FIG. 1.

The American Society for Testing and Materials [ASTM] has a standard test to determine if an Aluminum-Magnesium alloy is sensitized. The ASTM G67 test involves destructive testing of a sample coupon obtained from the ship structure. This test is destructive, complicated, expensive, and time-consuming. Recently, other means for testing the sensitization of a Aluminum-Magnesium alloy have become available. ElectraWatch, Inc. has developed a Degree of Sensitization (DoS) Probe which is a nondestructive tool currently approved by the U.S. Navy for quantitative material assessment of the 5456 series aluminum alloys found on many Navy ships. Use of the DoS Probe to determine sensitization of ship structure made from Aluminum-Magnesium alloy is non-destructive, can be performed on the ship, is very quick and relatively inexpensive compared to ASTM G67 testing. To date the DoS Probe has been used to conduct over 4,000 measurements on various Navy ships in support of modernization, maintenance, and repair efforts.

Stress corrosion cracking [SCC] is a serious problem in ships constructed [partially or completely] from 5XXX Aluminum-Magnesium alloys. Cracks in the superstructure of a ship can seriously weaken the superstructure leading to potential structural failure with all the associated potential for disaster. It is self-evident that cracks in the hull of a ship are a disaster waiting for an opportune time to occur. In addition, sensitized 5XXX portions of a ship can cause other problems. Ship repairs and/or modifications involving welding can be problematical when dealing with sensitized Aluminum-Magnesium alloys.

The Navy has created their own guidance on the weldability of sensitized 5XXX aluminum based on ASTM G67 testing [NAVSEA, 2013]. Under the Navy's guidance, material that tests between 0 and 20 mg/cm2 [under the ASTM G67 standard] can be welded using normal aluminum welding standards; material that tests over 20 mg/cm2 must meet critical welding requirements. Material that tests between 30 and 60 mg/cm2 must have the weld treated with cold working treatments to prevent re-cracking, and material that tests over 60 mg/cm2 must be replaced.

For these reasons, it is extremely desirable to have a means for determining when ship structures made from 5XXX alloys have been sensitized. Since it takes some time for these sensitized alloys to develop intergranular corrosion (IGC), if one knows that a particular portion of the ship structure has been sensitized, it is still possible to take corrective action before serious problems caused by SCC can occur. As noted above, testing using the ASTM G67 test or the recently available DoS Probe are available but both tests require complicated equipment and a certain amount of time and expense. In addition, both tests require trained personnel for successful testing. It would be extremely desirable to have a simple, quick test for sensitization which could be administered by relatively untrained personnel.

SUMMARY OF THE INVENTION

A simple, relatively inexpensive and quick test for sensitization of material made from 5XXX Aluminum-Magnesium alloy has been developed. The test can be administered by non-skilled personnel. As noted above, sensitized 5XXX Aluminum alloys contain Beta [$Al_3Mg_2$] precipitates which contain approximately 38% Mg which is significantly higher than the Al matrix, which for Al 5456 contains only approximately 5% Mg. Elemental Mg is thermodynamically less stable and kinetically more active than elemental Al. These characteristics make Beta [$Al_3Mg_2$] precipitates more susceptible to dissolution in low and neutral pH environments. Thus a solution comprising a moderately acidic chemical [pH of approximately 2] placed on a surface comprising sensitized 5XXX Aluminum alloy will dissolve any Beta [$Al_3Mg_2$] precipitates at grain boundaries preferentially to the surrounding Al matrix material. When the Beta [$Al_3Mg_2$] precipitates are dissolved into the chemical, it will change the pH of the chemical. If the solution with the moderately acidic chemical is mixed with an appropriate pH indicator [1-2] as the pH of the solution changes, the pH indicator will indicate the magnitude of this change.

Since non-sensitized 5XXX Aluminum alloys are less active than sensitized 5XXX Aluminum alloys, the same moderately acidic chemical with a pH indicator placed on non-sensitized 5XXX Aluminum alloy will take much longer to dissolve enough Mg to cause a corresponding change in the pH and thus an indication of this change by the pH indicator. This preferential dissolution can be utilized with a pH indicator to easily indicate when the 5XXX Aluminum alloy has large amounts of Mg present and thus whether it is sensitized or not.

The test is illustrated in FIGS. 2-4. FIG. 2 shows the application of the indicating chemical 2 to a sensitized test sample 4 which could be an area of a ship structure in situ [on the ship]. A light abrasion would be necessary to remove any protective coating on the area. FIG. 3 shows the same area after the passage of a certain, pre-determined amount of time. As is indicated by the change in the fill effect of indicating chemical 2 the pH indicator now indicates the presence of large amounts of dissolved Mg and thus that the area under the indicating chemical is sensitized. If the test sample 4 had not been sensitized, indicating chemical 2 would not have changed its pH in the same time or, at the least, not have had the same amount of pH change and the pH indicator would not have changed color.

The test is sensitive to time and temperature. If test sample 4 is heated [say to about 50° C.] the Mg dissolution into the chemical is expedited and the pH indicator will change color more quickly than if the test is performed at room temperature. It is possible, with the proper selection of an acid and a pH indicator combination to achieve a reliable test within a few minutes using a moderately acidic chemical.

It is noted that the chemical could be modified to include a thickening agent which would allow it to be sprayed onto a large surface and which would permit it to adhere to a vertical surface. Thus, a relatively large area could be tested in the same pre-determined period of time. Where the material is sensitized, the chemical would so indicate by changing color. In the areas where the material is not sensitized the absence of a color change would indicate the lack of sensitization. This is illustrated in FIG. 4 which illustrates the intersection of bulkhead 6 with deck 8. A relatively large portion 10 of bulkhead 6 has been cleaned to bare metal and sprayed with indicating chemical 12. The portions of bulkhead 6 that are sensitized are shown at 14.

It is noted that the indicating chemical does not have to be acidic. An alkaline-based indicating chemical will also produce the reaction. FIG. 5 shows a Pourbaix diagram for Aluminum [at 25° C.] with the stability regions for Magnesium superimposed thereon. FIG. 5 shows that both Aluminum and Magnesium will dissolve in a solution with a pH below about 4 [e.g. a mildly acidic solution]. FIG. 5 also shows that Aluminum and Magnesium will dissolve in a solution with a pH between about 8 and 11.

Non-sensitized 5XXX Aluminum alloys with no or low amounts of grain boundary beta phase contain much less Mg [~5% Mg] than sensitized 5XXX Aluminum alloys with large amounts of beta phase at grain boundaries [~38% Mg]. Elemental Mg is thermodynamically less stable and kinetically more active than elemental Al. Thus a solution comprising an alkaline chemical [pH of approximately 10] placed on a surface comprising sensitized 5XXX Aluminum alloy will form a passivation layer above beta phase [$Al_3Mg_2$] precipitates at grain boundaries. When the Beta phase[$Al_3Mg_2$] passivates, it will change the pH of the solution. If the solution with the alkaline chemical is mixed with an appropriate pH indicator [e.g. ~9-11], as the pH of the solution changes, the pH indicator will indicate the magnitude of this change.

It is noted that the test of this invention will indicate whether the material is sensitized or not. It may be possible with refinement of the chemical reaction to determine appropriate Degree of Sensitization ranges; however, the current test of the invention can also indicate at least some information on the Degree of Sensitization [DoS] depending upon the rate and severity of the corrosion reaction. Once it has been determined that a particular area is sensitized, the ASTM G67 or DoS Probe test can be applied to the specific sensitized areas to determine the degree of sensitization for those areas and then it will be possible to determine what type of repair (if any) is necessary.

It is noted that the test of this invention can provide at least some information on the Degree of Sensitization of a sample of 5XXX Aluminum alloy in the following manner. The amount of time it takes the indicating chemical to change color when applied to a sample is an approximate indication of the Degree of Sensitization of the sample. For example, when the indicating chemical is applied to a highly sensitized sample of 5XXX Aluminum alloy, the pH change [and thus the pH color change] will proceed more quickly during a given amount of time than the pH change will occur on a less sensitized sample of 5XXX Aluminum alloy. This assumes that the same amount of indicating chemical is applied to each sample and that the samples are at the same temperature.

FIG. 6 illustrates this relationship between elapsed time and the percentage of pH color change for 5 imaginary samples of 5XXX Aluminum alloy. The % pH color change is plotted on the abscissa against elapsed time plotted on the ordinate. For sample D, the amount of time taken to achieve a 100% pH color change was considerably less than the amount of time taken for Sample A to achieve the same pH color change. Sample B took slightly less time to achieve the same pH color change than Sample A and Samples C and D took slightly less time to achieve the same pH color change than did Sample B. Thus, it can be deduced from this example that sample D is the most highly sensitized of the four samples and has the highest Degree of Sensitization. It can likewise be deduced that sample A is the least highly sensitized sample and has the lowest Degree of Sensitization. Samples B and C have Degrees of Sensitization between those of sample A and sample D. With experience gained from a number of tests, the time elapsed for a given sample to reach a given percentage of pH color change can thus be correlated to the Degree of Sensitization of the sample. At the very least, it can be deduced that sample D should be tested [and soon] with a more accurate Degree of Sensitization test such as the ASTM-G67 test or the ElectraWatch, Inc. DoS Probe test referred to supra.

DETAILED DESCRIPTION

Figure 1:
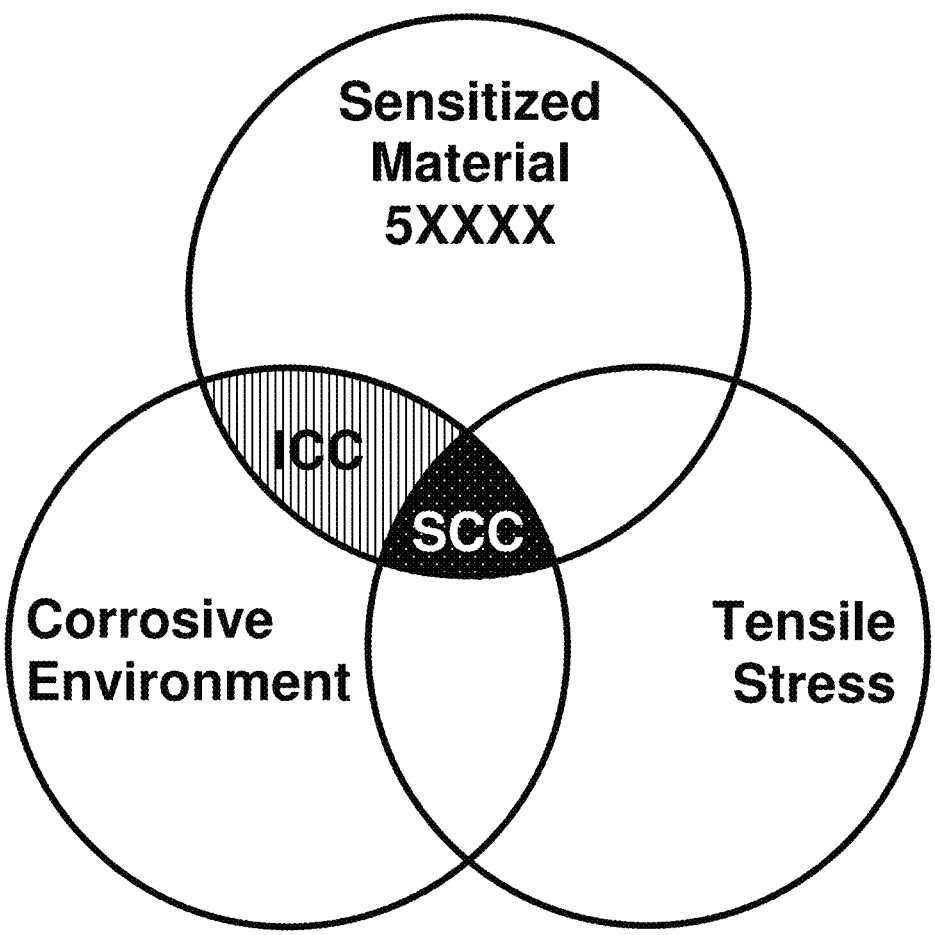
FIG. 1 illustrates the relationship between sensitization of 5XXX Aluminum alloy structures, intergranular corrosion (IGC) and stress corrosion cracking (SCC).
Figure 2:
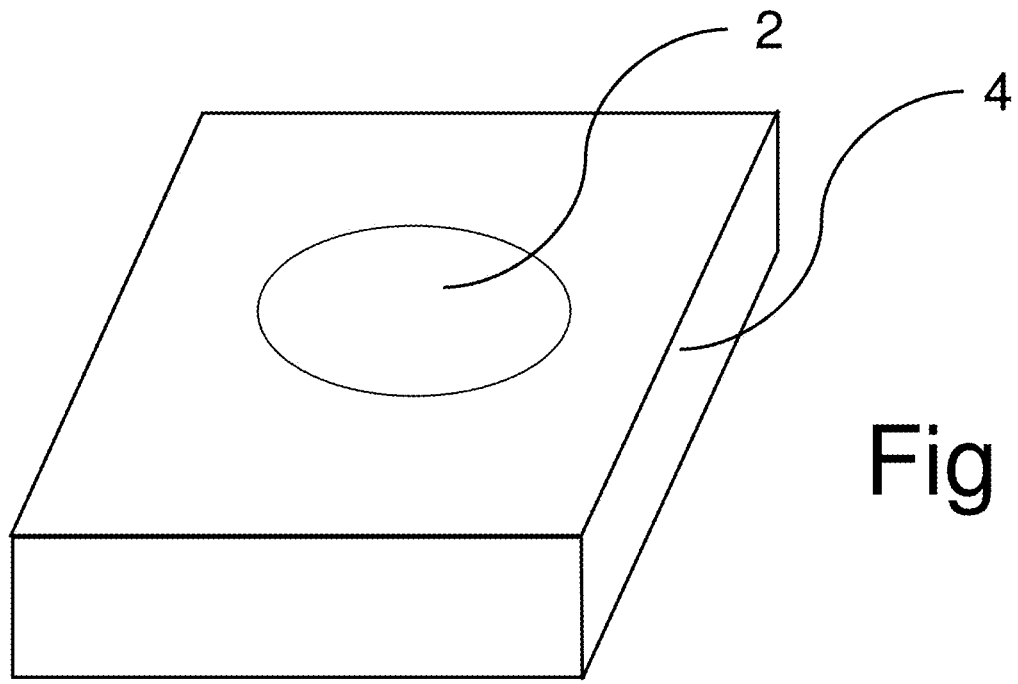
FIGS. 2 and 3 illustrate a first embodiment of the inventive sensitization test on a 5XXX Aluminum alloy sample coupon.
Figure 3:
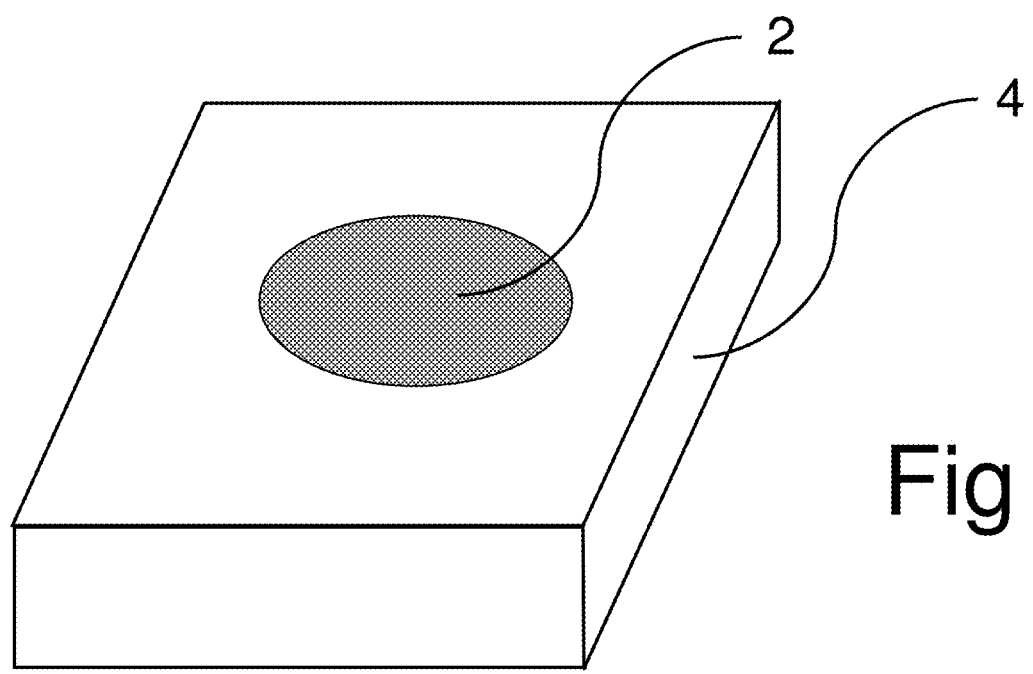
Figure 4:
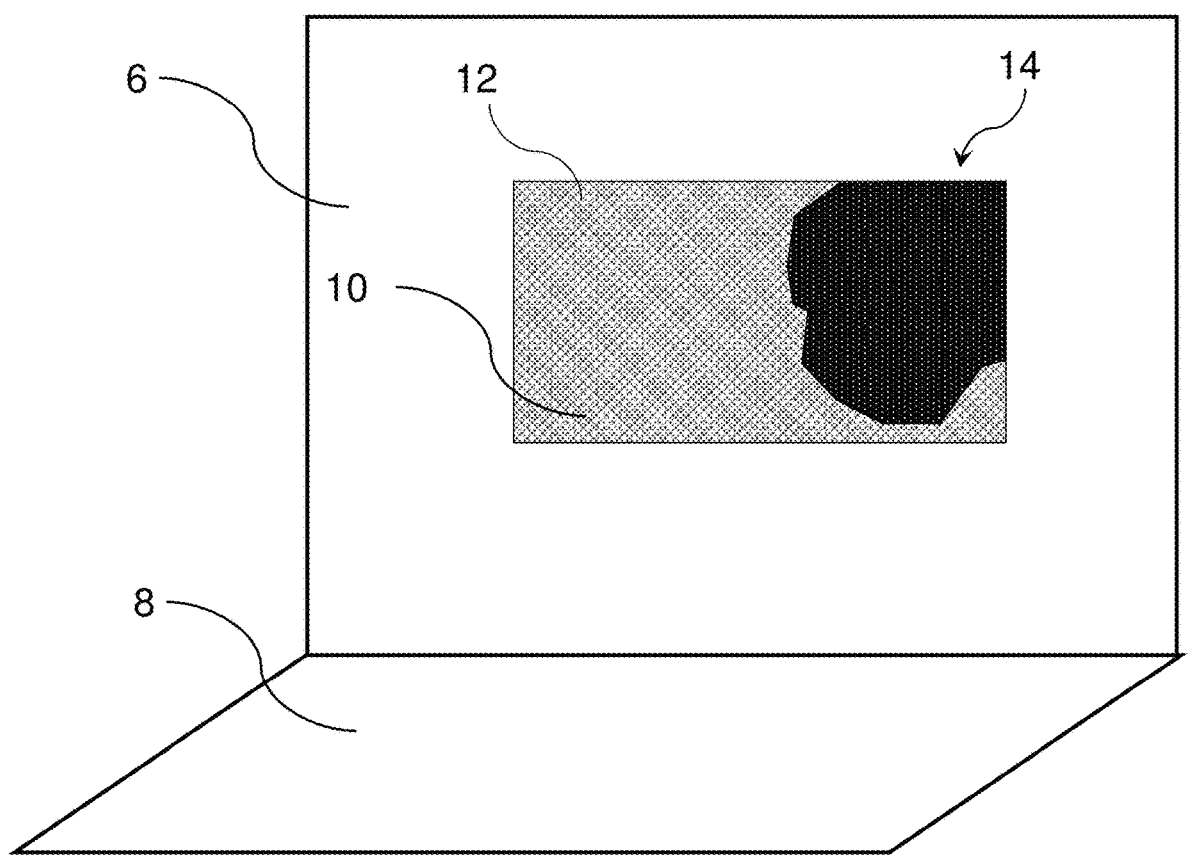
FIG. 4 illustrates a second embodiment of the inventive sensitization test being done in situ on the bulkhead of a ship.
Figure 5:
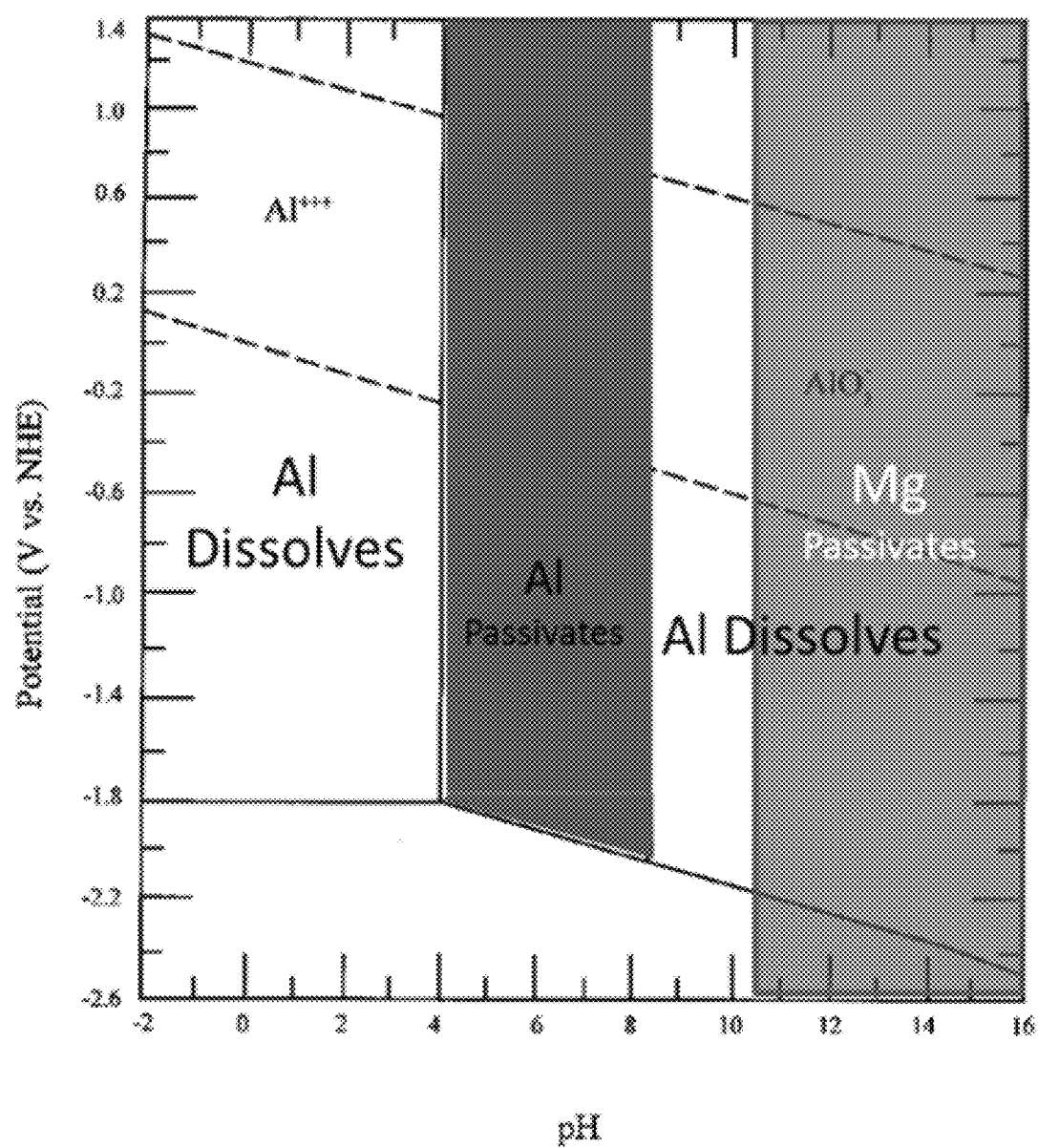
FIG. 5 shows a Pourbaix diagram for Aluminum [at 25° C.] with the stability regions for Magnesium superimposed thereon.
Figure 6:
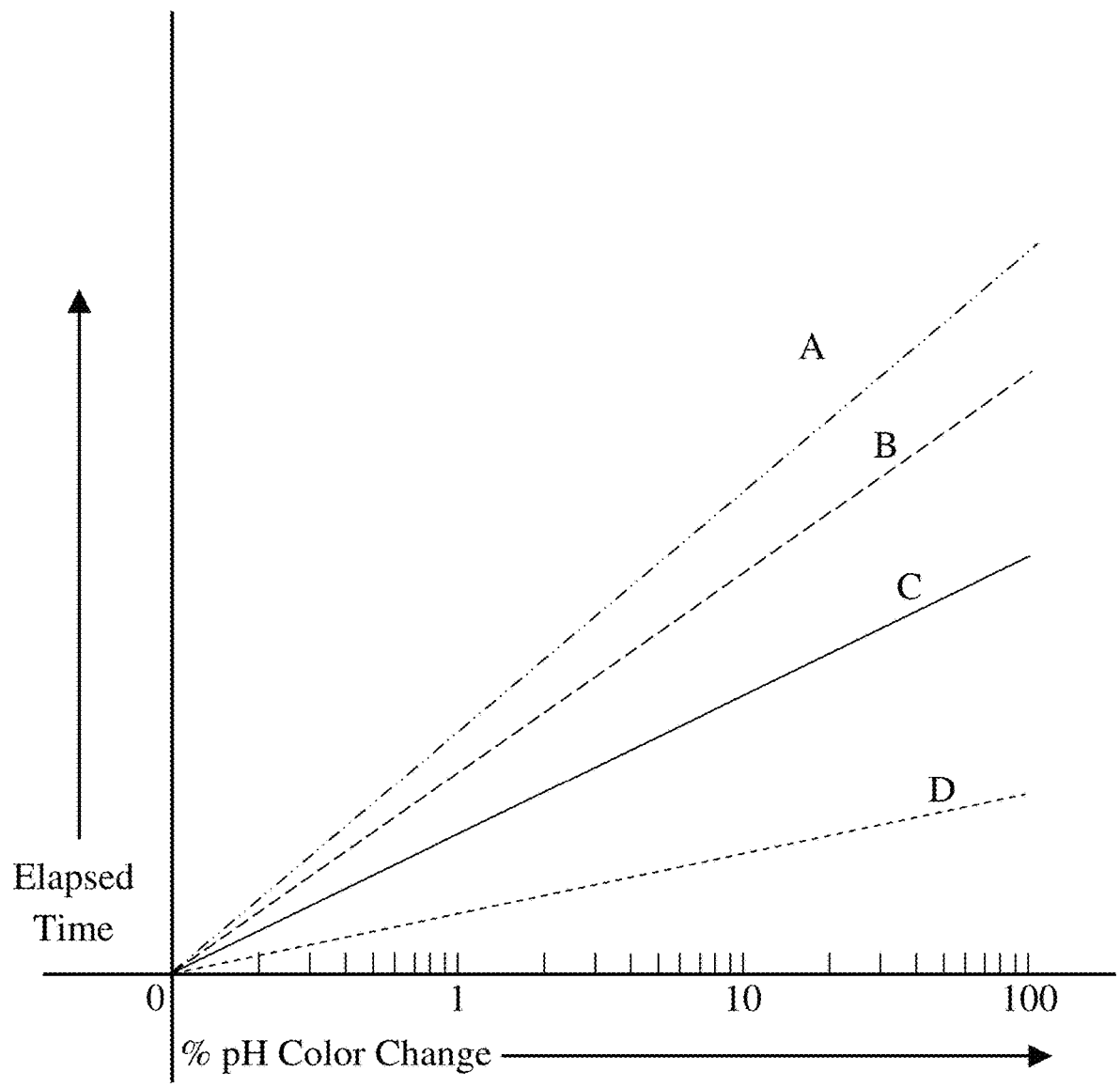
FIG. 6 illustrates how the inventive test can be used to determine or at least approximate the Degree of Sensitization of a sample of 5XXX Aluminum alloy.

In the first embodiment of the test, the material to be tested, either a sample coupon 4 such as shown in FIG. 2, or a specific portion of a larger structure such as ship bulkhead 6 shown in FIG. 4 is cleaned to bare metal. A light abrasion may be necessary to perform this cleaning step. The indicating chemical is then placed onto sample coupon 4 or sprayed on the specific area 10 being tested on bulkhead 6. For a vertical bulkhead such as 6 in FIG. 4, it may be necessary to mix the indicating chemical with a thickening agent as described supra. The reaction is allowed to continue for a pre-determined amount of time and any changes in the color of the indicating chemical are observed. A color comparison chart is utilized which has several color swatches therein to indicate what the color of the indicating chemical is at the start of the test and what color it is at the end of the test if the material being tested is sensitized. To generate the color comparison chart, the test is run on a sample coupon which is highly sensitized, for example, sensitized to correspond to an ASTM G67 standard of 60 mg/cm2. It is noted that according to US Navy standards, material that is sensitized to 60 mg/cm or greater according to the ASTM G67 test must be replaced. The elapsed time for this test is plotted against the observed color changes in the indicating chemical. The various colors that the indicating chemical turns at various amounts of elapsed time can then be placed on the color comparison chart as color swatches. Thus, when running a test in the field, comparison of the color achieved by the indicating chemical after a pre-determined elapsed time will indicate if the material being tested is sensitized and also give at least an approximation of the Degree of Sensitization of the material. Thus, if there is no observed change of color during the elapsed time, of the indicating chemical, it can be deduced that the material is not sensitized. On the other hand, if there is a change in the color of the indicating chemical, comparison with the color comparison chart swatches will indicate if the material is sensitized and also give an indication of the Degree of Sensitization [DoS]. If the test is being performed upon a specific area 10 of a large structure, such as ship bulkhead 6, it also possible to determine by where the change in color [shown at 14 in FIG. 4] occurs within the large area exactly which portions of area 10 are sensitized and which are not sensitized.

In the second embodiment of the test, the material to be tested, either a sample coupon 4 such as shown in FIG. 2, or a specific portion of a larger structure such as ship bulkhead 6 shown in FIG. 4 is cleaned to bare metal. The temperature of coupon 4 or area 10 is measured. The indicating chemical is then placed onto sample coupon 4 or sprayed on the specific area 10 being tested on bulkhead 6. To generate the color comparison chart used for this embodiment, the test is run on a sample coupon which is highly sensitized, for example, sensitized to correspond to an ASTM G67 standard of 60 mg/cm2. The test is repeated for several different temperatures corresponding to those expected for materials in the field which are to be tested. The elapsed time for this test for each selected temperature is plotted against the observed color changes in the indicating chemical. The various colors that the indicating chemical turns at various amounts of elapsed time can then be placed on the color comparison chart as color swatches. Thus, when running a test in the field, comparison of the color achieved by the indicating chemical after a pre-determined elapsed time will indicate if the material being tested is sensitized and also give at least an approximation of the Degree of Sensitization of the material. If there is no observed change of color, of the indicating chemical, it can be deduced that the material is not sensitized. If there is an observed change in the color of the indicating chemical, then the amount of change in color [determined using the color comparison chart swatches] and the time it took to reach the specific color observed can be used to estimate the DoS.

In the third embodiment of the test, the material to be tested, either a sample coupon 4 such as shown in FIG. 2, or a specific portion of a larger structure such as ship bulkhead 6 shown in FIG. 4 is cleaned to bare metal. The temperature of coupon 4 or area 10 is measured. The indicating chemical is then placed onto sample coupon 4 or sprayed on the specific area 10 being tested on bulkhead 6. Based on the measured temperature, the test is allowed to run for a certain amount of time. At the end of this pre-determined time, the final color of the indicating chemical is then used to estimate the DoS.

In the fourth embodiment of the test, the material to be tested, either a sample coupon 4 such as shown in FIG. 2, or a specific portion of a larger structure such as ship bulkhead 6 shown in FIG. 4 is cleaned to bare metal. The temperature of coupon 4 or area 10 is brought to and maintained at a pre-determined value [say approximately 50° C.]. The indicating chemical is then placed onto sample coupon 4 or sprayed on the specific area 10 being tested on bulkhead 6. Based on the controlled temperature, the test is allowed to run for a certain amount of time. At the end of this pre-determined time, the final color of the indicating chemical is then used to estimate the DoS. This embodiment of the test can be performed in less time than the other embodiments because, as noted supra, the test is sensitive to temperature and the pH indicator will change color more quickly at an elevated temperature than it will at room temperature.

The above-described embodiments are merely illustrative of the principles of the invention. Those skilled in the art may make various modifications and changes, which will embody the principles of the invention and fall within the spirit and scope thereof.

The invention claimed is:

1. A method of determining whether or not a portion of a metallic structure comprising 5XXX Aluminum alloy is sensitized comprising the steps of:
   cleaning the metallic structure portion to bare metal;
   applying an indicating chemical combined with a pH indicator to the portion of the metallic structure comprising 5XXX Aluminum alloy;
   allowing a pre-determined amount of time to pass; and,
   determining that said 5XXX Aluminum alloy is sensitized if a color change in the indicating chemical is observed within said pre-determined amount of time.

2. The method of claim 1 wherein the pH of the indicating chemical is less than or equal to 2.

3. The method of claim 1 wherein the pH of the indicating chemical is less than about 11 and greater than about 8.

4. The method of claim 1 wherein the pH of the indicating chemical is approximately 10.

5. The method of claim 1 wherein the metallic structure comprises a ship comprising 5XXX Aluminum alloy and the step of applying an indicating chemical to a portion of a metallic structure comprising 5XXX Aluminum alloy is performed in situ.

6. The method of claim 5 wherein the indicating chemical further comprises a thickening agent and wherein the step of applying an indicating chemical further comprises spraying the indicating chemical with said thickening agent therein upon a portion of the ship comprising 5XXX Aluminum alloy.

7. The method of claim 6 wherein the portion of the ship is a vertical bulkhead on a ship comprising 5XXX Aluminum alloy.

8. A method of determining the degree of sensitization of a portion of a metallic structure comprising 5XXX Aluminum alloy comprising the steps of:
   cleaning the metallic structure portion to bare metal;
   applying an indicating chemical combined with a pH indicator to the portion of the metallic structure comprising 5XXX Aluminum alloy:
   allowing a pre-determined amount of time to pass;
   further comprising plotting the color change in said indicating chemical against the amount of time necessary to obtain said color change and determining the degree of sensitization of the portion of the metallic structure comprising 5XXX Aluminum alloy from the plotting.

9. A method of determining the approximate degree of sensitization of a portion of a metallic structure comprising a particular 5XXX Aluminum alloy comprising the steps of:
   cleaning said portion of said metallic structure to bare metal;
   measuring the temperature of said portion of said metallic structure;
   placing an indicating chemical with a pH indicator therein on said portion of said metallic structure;
   allowing a certain amount of time to pass with said certain amount of time being selected based upon said measured temperature;
   further comprising plotting the color change in said indicating chemical against the amount of time necessary to obtain said color change and determining the approximate degree of sensitization of the portion of the metallic structure comprising 5XXX Aluminum alloy from the plotting.

* * * * *